(12) United States Patent
Lanois et al.

(10) Patent No.: US 9,247,933 B2
(45) Date of Patent: *Feb. 2, 2016

(54) BONE ANCHOR DELIVERY SYSTEM DEVICE AND METHOD

(71) Applicant: Valeris Medical, LLC, Marietta, GA (US)

(72) Inventors: Daniel Brian Lanois, Atlanta, GA (US); Bradford Lee Boone, Tulsa, OK (US); Ryan Eric Gursky, Tulsa, OK (US); James Calvin Johnson, Oklahoma City, OK (US); Bruce Scott Markman, Bixby, OK (US)

(73) Assignee: Valeris Medical, LLC, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/677,265

(22) Filed: Apr. 2, 2015

(65) Prior Publication Data

US 2015/0209026 A1 Jul. 30, 2015

Related U.S. Application Data

(63) Continuation of application No. 14/527,043, filed on Oct. 29, 2014.

(60) Provisional application No. 61/928,088, filed on Jan. 16, 2014.

(51) Int. Cl.
*A61B 17/04* (2006.01)

(52) U.S. Cl.
CPC ....... *A61B 17/0401* (2013.01); *A61B 2017/044* (2013.01); *A61B 2017/0409* (2013.01); *A61B 2017/0441* (2013.01); *A61B 2017/0445* (2013.01)

(58) Field of Classification Search
CPC .......... A61B 17/0401; A61B 2017/0409; A61B 2017/0403; A61B 2017/0404; A61B 2017/0406; A61B 2017/0412; A61B 2017/0414
USPC ......................................... 606/232
See application file for complete search history.

(56) References Cited

U.S. PATENT DOCUMENTS

| | | | | |
|---|---|---|---|---|
| 5,258,016 A | * | 11/1993 | DiPoto | A61B 17/0401 606/104 |
| 5,626,612 A | * | 5/1997 | Bartlett | A61B 17/0401 606/232 |
| 6,544,281 B2 | | 4/2003 | Elattrache et al. | |
| 7,329,272 B2 | | 2/2008 | Burkhart et al. | |
| 7,585,311 B2 | | 9/2009 | Green et al. | |

(Continued)

*Primary Examiner* — Thomas McEvoy
(74) *Attorney, Agent, or Firm* — David L. King

(57) ABSTRACT

A bone anchor delivery system device (10) has a retractable punch driver assembly and a locking mechanism (32). The punch driver assembly has a retractable punch shaft (30) and a guide (20) for receiving the retractable punch shaft (30). The guide (20) is rotatable relative to the punch shaft (30) and the shaft has an extended length with bone penetrating tip (35) at a first end (33). The locking mechanism (32) for locking the retractable punch shaft (30) from linear movement and rotational movement relative to the guide (20) is positioned at an opposite second end. The retractable punch shaft (30) has a reduced diameter end (33) extending from the tip (35) toward a shoulder stop for receiving a releasable punch (12). The releasable punch (12) has a hollow opening for receiving the reduced diameter end (33) of the punch shaft (30). The punch (12) is profiled to pierce and form a bone anchor hole.

25 Claims, 8 Drawing Sheets

(56) References Cited

U.S. PATENT DOCUMENTS

| | | |
|---|---|---|
| 7,993,369 B2 | 8/2011 | Dreyfuss |
| 8,114,127 B2 | 2/2012 | West |
| 8,430,909 B2 | 4/2013 | Dreyfuss |
| 8,663,279 B2 | 3/2014 | Burkhart et al. |
| 2008/0275431 A1* | 11/2008 | Stone ................. A61B 17/0401 |
| 2010/0292732 A1* | 11/2010 | Hirotsuka .......... A61B 17/0401 606/1 606/232 |
| 2012/0150226 A1 | 6/2012 | Burkhart |
| 2014/0277129 A1* | 9/2014 | Arai .................... A61B 17/0401 606/232 |
| 2014/0364906 A1* | 12/2014 | Palese ................ A61B 17/0401 606/232 |

* cited by examiner

BONE ANCHOR DELIVERY SYSTEM DEVICE AND METHOD

RELATED APPLICATIONS

The present application is a continuation of co-pending U.S. application Ser. No. 14/527,043 filed Oct. 29, 2014 entitled "Bone Anchor Delivery System Device And Method".

TECHNICAL FIELD

The present invention relates to methods and instruments for fixation of sutures and tissue to bone, more particularly to a bone anchor system for securing sutures for attachment of soft tissue like ligament and cartilage to bone.

BACKGROUND OF THE INVENTION

The use of bone screw anchors to hold sutures is a widely accepted practice in shoulder or knee repair and fixation of soft tissue such as ligaments, cartilage and tendons to bone. Ideally the suture anchor is easy to install and provides a solid reliable way to fix the sutures to the bone. The bone has a hard outer cortical shell with a softer underlying region of cancellous bone tissue. The anchor must hold sutures after thousands of repetitive motions tensioning and relaxation until the ligament or tendon repair has time to heal and secure itself to the bone and muscle tissue.

Older style bone anchors had an external eyelet to allow the sutures to be fed through after the screw was driven into the bone. This left the eyelet exposed in the soft muscle tissue.

Later versions of bone anchors have the sutures inserted inside the screw tip well inside the bone. This allows the screw outer end to stay flush with the cortical bone outer surface. The sutures can pass inside in some hollow screws from the tip to the outer surface. Others have the sutures held at the tip end and are exterior held between the anchor screw threads and the bone. In some suture anchor systems there is a self-driving feature that has a stainless steel punch with a steel tip that can be malleted into the bone. This design leaves the tip end trapped in the bone opening meaning the patient has a small steel tip in his shoulder or knee.

Ideally the procedure should insure the bone anchor is easily installed leaving no punch tip fragments in the body and more particularly avoiding having steel tips or metal fragments left in the bone.

The present invention provides a threaded bone anchor that is easy to install wherein the sutures are held without leaving metal fragments or metal tips and, furthermore, this is accomplished with a unique insertion tool and anchor screw assembly to make the procedure simple and convenient to use.

SUMMARY OF THE INVENTION

A bone anchor delivery system device has a retractable punch driver assembly and a locking mechanism. The punch driver assembly has a retractable punch shaft and a guide for receiving the retractable punch shaft. The guide is rotatable relative to the punch shaft and the shaft has an extended length with bone penetrating tip at a first end. The locking mechanism for locking the retractable punch shaft from linear movement and rotational movement relative to the guide is positioned at an opposite second end. The retractable punch shaft has a reduced diameter end extending from the tip toward a shoulder stop for receiving a releasable punch. The releasable punch has a hollow opening for receiving the reduced diameter end and bone penetration tip at the first end. The punch is profiled at a first end to be complimentary to the tip to pierce and form a bone anchor hole and has an opposite second end for abutting the shoulder of the punch shaft.

Preferably, the reduced diameter end of the punch shaft and the punch have a snap lock feature to hold the punch. The snap lock feature allows for rotational movement of the punch relative to the punch shaft. The releasable punch has a plurality of openings for threading one or more sutures. In one embodiment, the releasable punch openings are one or more pairs of slots sized to receive a plurality of sutures.

The bone anchor delivery system device further has a releasable threaded bone anchor. The threaded bone anchor is hollow having an opening attachment onto the guide. The bone anchor extends from a first leading end to an opposite second end abutting the guide. The guide has a reduced end having a releasable snap locking feature and the bone anchor has a complimentary releasable lock for holding the bone anchor to the guide. The bone anchor delivery system device has the punch shaft extending past the guide to the shoulder second end by a length L, wherein L is equal to the length of the bone anchor. In the use of the anchor delivery system device, the punch end tip penetrates the bone creating an opening or hole extending to a depth wherein the bone anchor is positioned adjacent above the bone opening and thereafter threaded into the bone opening or hole.

The bone anchor delivery system device further has a handle assembly. The handle assembly has a lower portion rotatable about the guide and an upper portion fixed to the guide and wherein the upper portion is rotatable independent of said lower portion. The upper portion has an impact end for impacting the handle assembly to drive the punch through bone using a mallet if needed. The upper handle has a slot to receive the locking mechanism to prevent linear movement of the retractable punch shaft. The punch shaft is a rod or wire and the locking mechanism is integrally formed as part of the rod or wire at a second distal end by a bending of the punch shaft to form a spring like lock snap end to fit into the upper handle slot locking the punch shaft in place. The spring like snap end when released from the slot allows the punch shaft to move linearly in an elongated slotted opening in the upper handle to retract the punch shaft. Rotation of the upper handle after the lock mechanism is released allows the bone anchor to be driven into said bone opening formed by the punch. The punch is released from the punch shaft end by withdrawing of the punch shaft end and the abutting the end of the driven bone anchor. The release of the initial retractable punch assembly occurs by pulling past the snap feature in the guide and the bone anchor. The lower handle provides a non-rotatable hand grip for stabilizing the device as the upper handle is rotated. Preferably, the punch and the bone anchor are non-metal. The bone anchor or the punch can be made of synthetic or natural non-metal material. Either can be made of a plastic material, the plastic material is preferably PEEK. The punch or bone anchor also can be made of a bioabsorbable material. The bone anchor can be made of cortical bone.

DEFINITIONS

As used in this specification, the singular forms "a," "an" and "the" include plural referents unless the context clearly dictates otherwise. Thus, for example, the term "a material" is intended to mean one or more materials, or a combination thereof.

BRIEF DESCRIPTION OF THE DRAWINGS

The invention will be described by way of example and with reference to the accompanying drawings in which:

FIG. 5A shows the step of locating the insertion position.

FIG. 5B shows the step of driving the punch to depth.

FIG. 5C shows the steps of releasing the lock mechanism and driving the anchor by rotation of the device until flush with the bone surface.

FIG. 5D shows the step of pulling back the device to release it from the bone anchor.

DETAILED DESCRIPTION OF THE INVENTION

Figure 1:
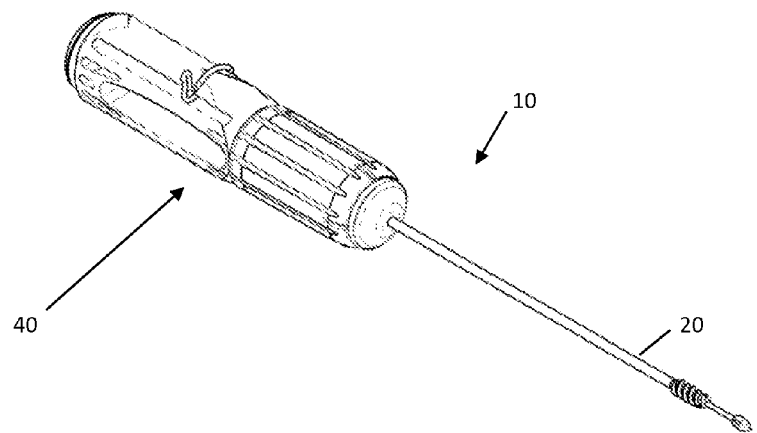
FIG. 1 shows a perspective view of the bone anchor delivery system device of the present invention.
Figure 2A:
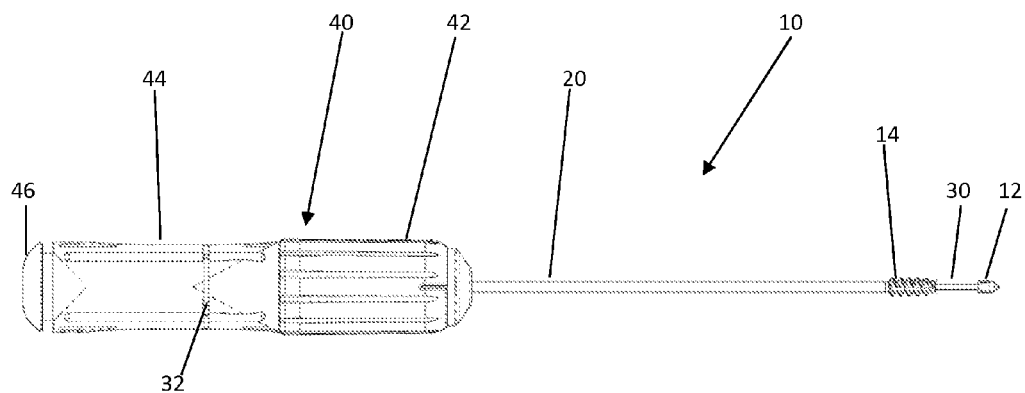
FIG. 2A is a first side plan view of the device of FIG. 1.
Figure 2B:
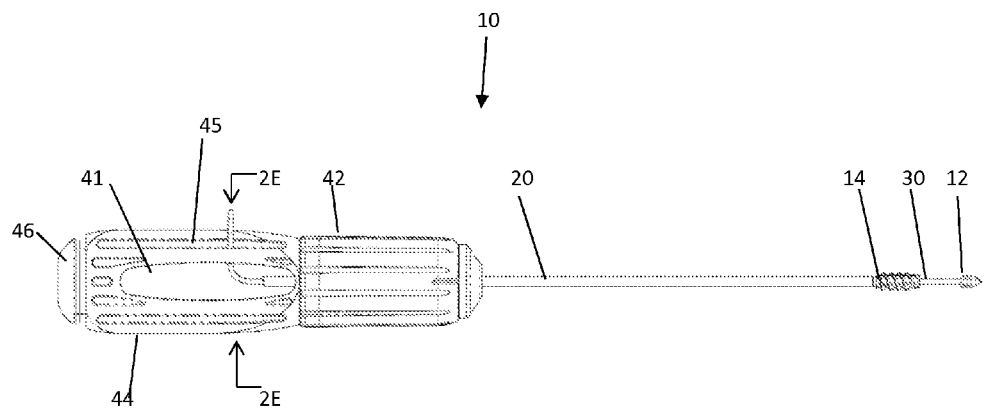
FIG. 2B is a second side plan view of the device in FIG. 2A rotated 90 degrees.
Figure 2C:
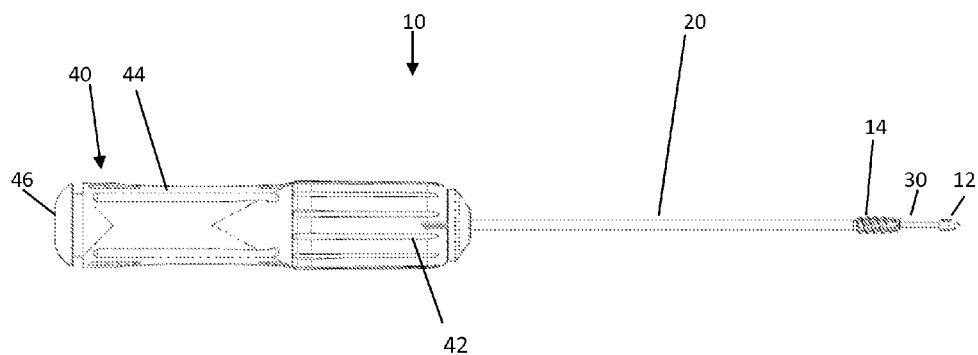
FIG. 2C is a third side plan view of the device of FIG. 2A rotated an additional 90 degrees.
Figure 2D:
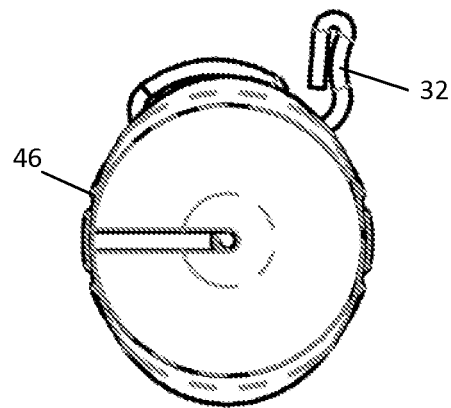
FIG. 2D is an end view of the device of FIG. 1.

With reference to FIG. 1, a perspective view of a bone anchor delivery system device 10 is illustrated. As further shown in FIGS. 2A-2D, the device 10, as illustrated, has a two part handle 40, a lower handle 42 which is rotatable about a guide 20 and an upper handle 44 which is fixed to the guide 20. As further illustrated in FIG. 1, the guide 20 extends from the handle 40 located at a second end to a leading first end. The guide 20, as illustrated, is hollow and has a punch shaft 30 extending from inside the guide 20 to the leading first end. At the very tip 35 of the leading first end 33 of the guide 20 is illustrated a releasable punch 12. Extending further up the punch shaft 30 is illustrated a bone anchor 14. The bone anchor 14 preferably has a length that is approximately equal to the length of that part of the shaft 30 extending beyond the guide 20, as illustrated. The bone anchor 14 preferably is a threaded screw structure hollow on the inside which allows the punch shaft 30 to extend through the bone anchor 14, as illustrated. At the handle end 40, the guide 20 is shown extending partially into a slotted opening 41 of the upper handle 44 as illustrated in FIG. 2B. The punch shaft 30 extends beyond the guide 20 and is bent and wrapped around the handle 44 as illustrated. This punch shaft 30 extends from the slot 41 upwardly and at the bend is wrapped around the upper handle 44. This bend forms a spring like stop mechanism 32 that fits into slots 43 and 45 in the handle 44. This prevents the punch shaft 30 from moving linearly or rotating relative to the device 10. As further shown, the upper handle portion 44 has a rounded somewhat flattened head or end 46. This flattened end 46 is adjacent a groove portion above the upper handle 44. This end 46 provides a surface on which a surgeon may take a mallet and drive the device into bone.

Figure 2E:
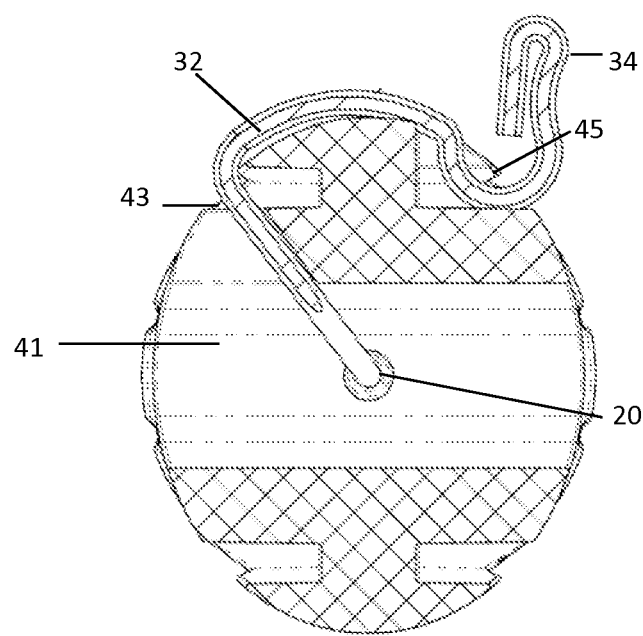
FIG. 2E is a cross sectional view of the device taken along lines 2E-2E of FIG. 2B.
Figure 2F:
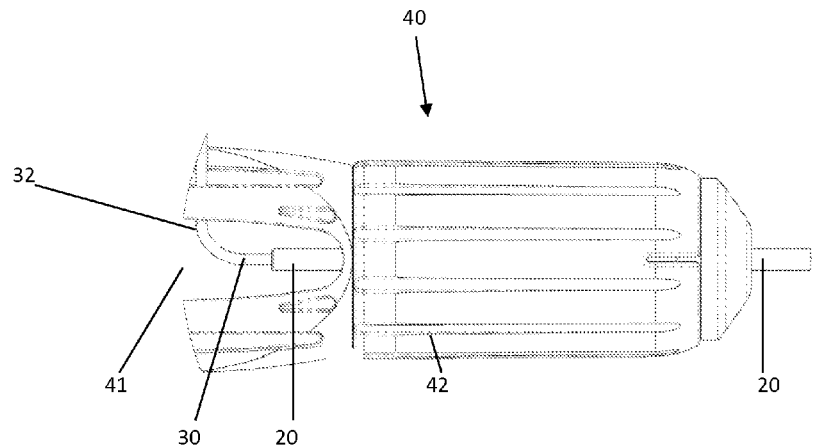
FIG. 2F is an enlarged side view showing a portion of the device.

The punch shaft 30 is best illustrated in the cross sectional view FIG. 2E wherein the punch shaft 30 is shown bent into the configuration making the spring type tension locking mechanism 32 that is easily snapped into position into the upper handle 44 as illustrated in FIG. 2E. To release the punch shaft 30 from the slots 43 and 45 holding locking mechanism 32, the surgeon simply pushes on the folded over end 34 as illustrated in FIG. 2E which will release the tension on the spring lock mechanism 32 and allow the punch shaft 30 to rotate back into the slot opening 41, when this occurs the punch shaft 30 is free to move linearly up or down relative to the guide 20.

Figure 3A:
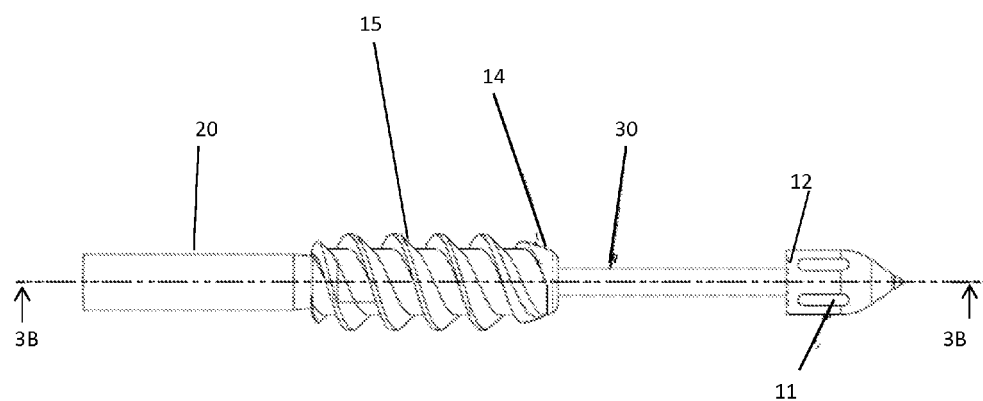
FIG. 3A is an enlarged side view of the leading end portion of the device taken from FIG. 2B.

With reference to FIGS. 3A, 3B, 4A and 4B, the leading end of the retractable punch driver assembly is illustrated. The retractable punch driver assembly comprises the guide 20 which is a hollow cylindrical tube into which the punch shaft 30 fits and extends from the locking mechanism 32 through the guide 20 and extends beyond the guide by a distance L. This distance L preferably extends sufficiently that the threaded bone anchor 14 fitted over an end 22 of the guide 20 as illustrated occupies approximately the same distance L between the end of the punch 12 and the guide 20. By providing the threaded bone anchor 14 of a length approximately equal to this extension of the punch shaft 30, it is possible to drive the punch 12 into the bone and leave the threaded bone anchor 14 above the bone surface. This enables the bone anchor 14 to be then rotationally driven into the bone opening created by the punch 12 once the device 10 has punched an opening into the bone. As shown in FIG. 3A, the punch 12 has a plurality of openings 11 to accept or receive sutures (not illustrated). As shown, these openings 11 can be slots to accommodate several sutures if so desired, preferably the sutures are threaded into and extend from one slot 11 inside the punch 12 through the other slot 11 to create a fixation of the suture within the punch 12, the ends of the suture being outside the device 10.

Figure 3B:
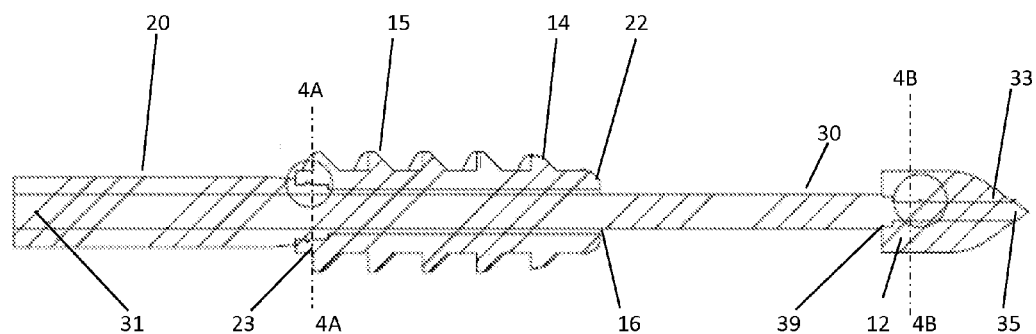
FIG. 3B is a cross sectional view of the leading end portion of the device taken along lines 3B-3B of FIG. 3A.

With reference to FIG. 3B, it is important to look at the punch 12 as it has a hollow opening for receiving the reduced diameter leading end 33 of the punch shaft 30. The end 33 of the punch shaft 30 is sharpened to a point at the tip 35 as illustrated. This reduced diameter end 33 preferably has a small ring 37 located between a shoulder 39 of the larger diameter portion 31 of the punch shaft 30 and the tip 35. This ring 37 as illustrated in FIG. 4B creates a snap locking feature. The punch 12 has a complimentary groove 13 that fits into the snap locking feature ring 37. As shown the punch 12 extends up to and abuts the larger diameter portion 31 of the punch shaft 30. On assembly, the snap feature ring 37 receives a groove 13 in the punch 12. Alternatively, a groove could be provided in the end 33 of the punch shaft 30 and a protrusion provided in the punch 12; however it is believed stronger that the punch 12 be provided with the groove 13 and the end 33 have a protrusion ring 37 on it. As illustrated, this ring 37 in connection with the groove 13 creates a releasable snap lock feature that enables the punch 12 to be placed over the tip 35 and end 33 snapped into position and held there. This prevents the punch 12 from slipping off inadvertently and is important that it be easily releasable once the punch 12 has been driven into the bone with the sutures in place in the slotted openings 11, as will be discussed later.

Figure 4A:
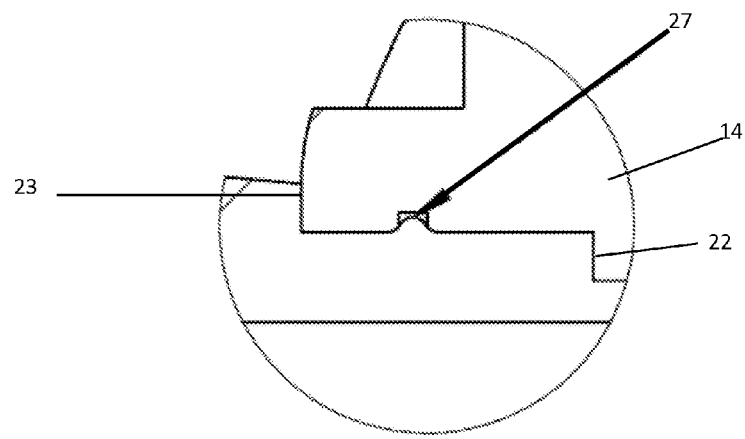
FIG. 4A is an enlarged view of the releasable snap retention feature of the threaded bone anchor and the guide taken from FIG. 3B.
Figure 4B:
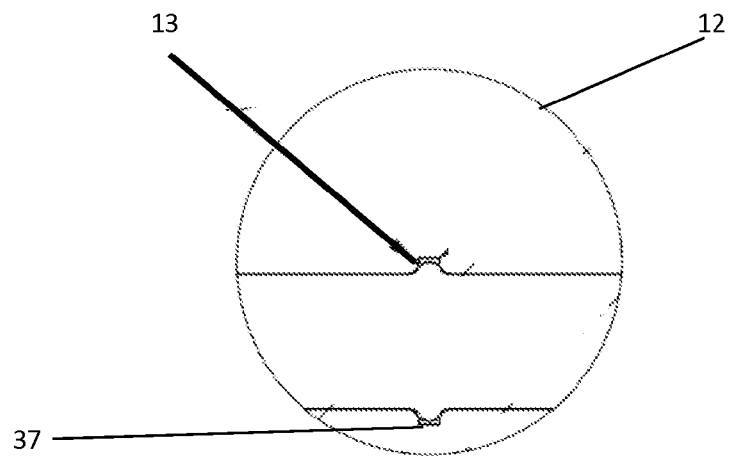
FIG. 4B is an enlarged view of the punch shaft tip releasable snap retention feature taken from FIG. 4A.

With reference to FIGS. 3B and 4A, the guide 20 extending over the punch shaft 30 has a one or more flat surfaces 22 at a leading or first end of the guide 20 and the bone anchor 14 similarly has one or more flat surfaces 16 complimentary to fit in a non-rotational fashion such that the bone anchor 14 is secured directly to the guide 20, preferably the guide 20 can be machined to a square and the anchor will have a square opening. The guide 20 further has a snap lock feature 27 at a reduced diameter end of the guide 20. This snap feature is a ring 27 similar to the snap feature 37 provided on the punch 12 and provides a protrusion or ring 27 around the reduced diameter portion 23 of the guide 20 that enables the bone anchor 14 to snap onto and be held there so that it is retained in this position as an assembly. This retention is releasable with a small amount of pressure enabling the bone anchor 14 to be released from the device 10 upon insertion into the bone. As shown, the bone anchor 14 preferably uses double helix tapered threads 15 that are sufficiently large to allow the bone anchor 14 to enter into the opening created by the punch 12 and to aggressively hold the anchor 14 into position in the cortical bone. It is important to note that the punch shaft 30 has an extended fixed distance that allows for punching the punch 12 a controlled depth leaving a length equal to the length L of the anchor 14. As discussed, it is important that the extension extend beyond the leading end of the bone anchor 14 by a distance at least equal to the total length of the bone anchor itself. Preferably, the tip 35 of the punch shaft 30 and the entire punch shaft 30 is made of stainless steel. The sharpened tip 35 assists in penetrating the bone along with the punch 12. It is preferable that the punch 12 and the bone anchor 14 be made of non-metal. Alternatively, while the anchor 14 and punch 12 could be made of metal, but it has been found that leaving remnants of metal in bone is not a preferred practice, and therefore, it is believed that a synthetic material such as plastic, preferably polyether ether ketone (PEEK) and or a bioabsorbable material would be preferred. The threaded bone anchor 14 itself may even include a bio-absorbable or natural material such as cortical bone. These and other possible materials are easily used in the manufacture of this device 10. It is even possible that natural compositions can be molded or cemented together in such a fashion that the punch itself can be made of a natural composition with the assistance of certain cements that would enable the punch 12 to be absorbed readily into the body, if so desired.

As shown, the punch 12 has a complimentary leading end that matches to the sharpened tip 35 of the end 33 such that upon hole penetration, the entire punch 12 has a diameter sufficient that it will allow the leading edge of the bone anchor 14 to engage the opening to initiate threading into the hole to secure the bone anchor 14 into the hole created by the punch 12.

Figure 5A:
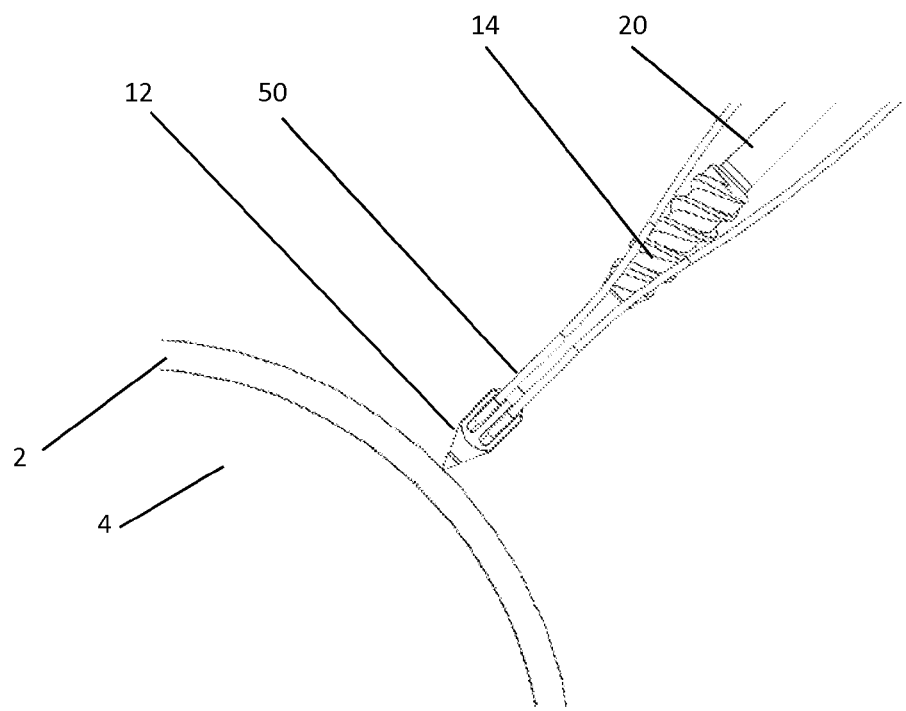
FIGS. 5A-5D illustrate the method of using the device to install the bone anchor of the present invention with sutures.
Figure 5B:
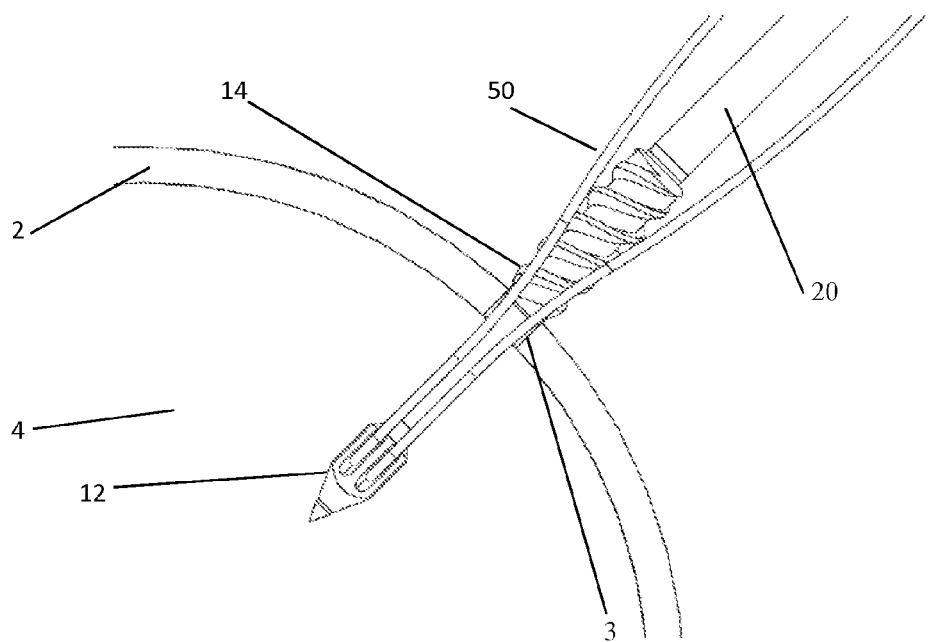
Figure 5C:
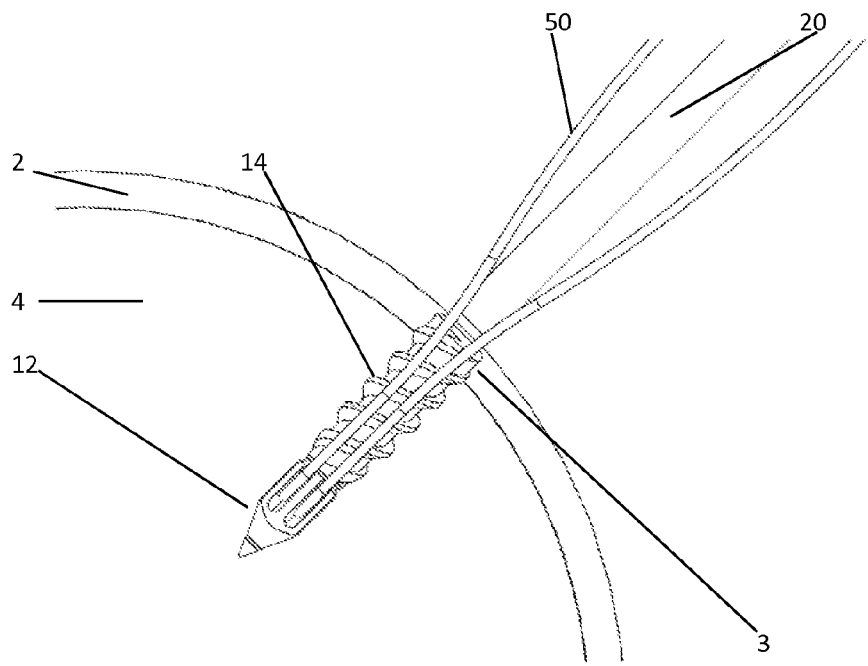
Figure 5D:
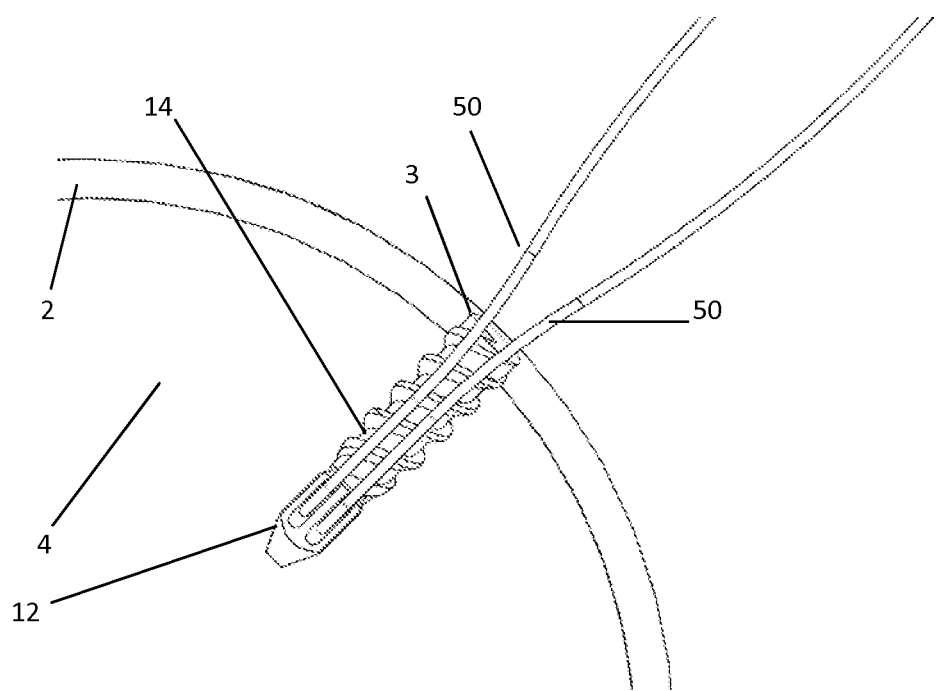

To better understand how the invention is used, reference is made to FIGS. 5A-5D. It is important to note that the surgeon should locate the position in which he wants the bone anchor 14 inserted. The bone anchor 14 with sutures 50 passed through slots 11 of the punch 12 will be positioned on the delivery device 10 and oriented in the desired direction the punch 12 is to penetrate into the bone 2. Once this position is secured, the surgeon can push and or use a mallet to punch to the desired depth. As shown in FIG. 5B, when the punch 12 achieves the desired depth, the anchor 14 is positioned directly above the opening at the outer surface of the cortical bone 2. The sutures 50 will be extending along the sides of the anchor 14, as illustrated. The sutures 50 can preferably be held off to one side or the other as they are retained in the punch 12 at the bottom of the hole 3 just created. The surgeon can then release the lock mechanism 32 of the punch shaft 30 and rotate the upper handle 44 of the device 10 such that the bone anchor 14 can be threadingly engaged and driven into the opening 3 in cortical bone 2 and cancellous bone 4 until it is flush with the surface of the cortical bone 2. As the surgeon is rotating the device 10, the two part handle 40 provides an optimal way for the surgeon to hold the lower handle 42 stationary as it free to rotate relative to the rotation of the guide 20 and the upper handle 44. The upper handle 44 being fixed to the guide 20 allows the lower handle 42 to be held in the non-rotatable fashion as the surgeon rotates the upper handle 44 thereby driving the bone anchor 14 into the bone 4. As the bone anchor 14 is being driven into the bone 4, the punch shaft 30, being released from the locked position, is free to linearly move outwardly relative to the bone opening. During this movement, the punch 12 can be released at any time. The snap release feature 37 is easily overcome by the resistance of the bone tissue 4. Alternatively, the punch 12 could, if the tissue 4 is very soft, continue to ride up the punch shaft 30 as it moves outward during the rotation and the driving of the bone anchor 14, such that, when the punch bottoms against the bone anchor 14, it will automatically release from the shaft 30. Once the bone anchor 14 is flush at the bone surface the surgeon simply pulls back and the snap release feature 27 on the guide holding the bone anchor 14 will similarly release allowing the entire device 10 to be pulled free. The beauty of this inventive device 10 is that the entire drive assembly is pulled free of the punch 12 and anchor 14 in such a fashion that no remnants of the punch driver assembly are left in the body. In this way, when the bone anchor 14 and punch 12 are made of non-metallic material, it is possible that the bone anchor 14 and punch 12 can be delivered in a relatively simple straightforward way wherein the entire drive device 10 excepting the punch 12 and anchor 14 is pulled out free of the patient leaving no metallic materials in the patient.

In almost all other conventional bone anchor delivery systems, the surgeon is required to hold a handle and rotate the device and the entire device rotates as the bone anchor is being positioned into the bone. When this occurs, the surgeon has no ability to either stabilize the device as provided in the present invention and further by being gloved, the surgical gloves have a tendency to wrap about the rotating prior art devices as they are being rotated, if the surgeon is attempting to hold onto the device with his other hand as he is rotating the device to anchor a bone anchor.

With the present invention, the gloved hand of the surgeon is held on a non-rotating lower handle portion 42 of the two part handle 40 as the upper handle portion 44 of the handle 40 is rotated, thereby driving the bone anchor 14. While this is a simple innovation, it is believed significant in that the surgeon can stabilize the bone anchor 14 preventing it from wobbling using two hands; one hand strictly for stabilization as the other hand provides rotation. More importantly, it is designed so that the surgeon's glove does not get wrapped or otherwise pinched into the rotating portions of the device. No other prior art device is known to have such a feature.

Furthermore, to the unique simplicity of the device 10 wherein the punch shaft 30 is made basically of a single stainless steel wire that has a machined leading end 33 sharpened to a point at the tip 35 of the reduced diameter and extends upwardly to an end where the wire is bent and formed to form a locking mechanism 32 that locks into slots 43, 45 in the upper handle 44. This locking feature being integral to the wire makes it a very low cost structure. Fundamentally, the device 10 is made of a guide 20, a punch shaft 30 and two handle portions 42, 44. The handle portions are plastic molded parts. This provides for a reasonably low cost, if not very low cost, bone anchor delivery system. The bone anchors 14 themselves can be small plastic components as well. This means that the surgeon will be able to use this device and throw it away if so desired due to its significant simplicity and low cost construction.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone anchor delivery system device comprising:
   a retractable punch driver assembly, the punch driver assembly having a retractable punch shaft and a guide for receiving the retractable punch shaft, the guide being rotatable relative to the punch shaft and the shaft having an extended length with bone penetrating tip at a first end; and
   a locking mechanism for locking the retractable punch shaft from linear movement and rotational movement relative to the guide at an opposite second end;
   a handle assembly, the handle assembly having a lower portion rotatable about the guide and an upper portion fixed to the guide and wherein the upper portion is rotatable independent of said lower portion, the upper portion has a slot to receive the locking mechanism to prevent linear movement of the retractable punch shaft; and
   wherein the punch shaft is a rod or wire and the locking mechanism is integrally formed as part of the rod or wire at a second distal end by a bending of the punch shaft to form a spring like lock snap end to fit into the slot of the upper portion locking the punch shaft in place.

2. The bone anchor delivery system device of claim 1 wherein the retractable punch shaft has a reduced diameter end extending from the tip toward a shoulder stop for receiving a releasable punch, the releasable punch having a hollow opening for receiving the reduced diameter end and bone penetration tip at the first end profiled to be complimentary to the tip and an opposite second end for abutting the shoulder stop of the punch shaft.

3. The bone anchor delivery system device of claim 2 wherein the reduced diameter end of the punch shaft and the punch have a snap lock feature to hold the punch, the snap lock feature allows for rotational movement of the punch relative to the punch shaft.

4. The bone anchor delivery system device of claim 1 wherein the releasable punch has a plurality of openings for threading one or more sutures.

5. The bone anchor delivery system device of claim 4 wherein the releasable punch openings are one or more pairs of slots sized to receive a plurality of sutures.

6. The bone anchor delivery system device of claim 3 further comprises a releasable threaded bone anchor, the threaded bone anchor being hollow having an opening for attachment onto the guide, the bone anchor extending from a first leading end to an opposite second end abutting the guide.

7. The bone anchor delivery system device of claim 6 wherein the guide has a reduced end having a snap lock feature and the bone anchor has a complimentary releasable lock for holding the bone anchor to the guide.

8. The bone anchor delivery system device of claim 7 wherein rotation of the upper portion after the lock mechanism is released allows the bone anchor to be driven into a bone opening formed by the punch.

9. The bone anchor delivery system device of claim 8 wherein the punch is released from the punch shaft end by withdrawing of the punch shaft and abutting the leading end of the driven bone anchor.

10. The bone anchor delivery system device of claim 9 wherein the release of the initial retractable punch assembly occurs by pulling past the snap lock feature in the guide and the bone anchor.

11. The bone anchor delivery system device of claim 8 wherein the lower portion provides a non-rotatable hand grip for stabilizing the device as the upper portion is rotated.

12. The bone anchor delivery system device of claim 6 wherein the punch shaft extends past the guide and the leading end of the bone anchor when the bone anchor is attached and abutted to the guide at the second end by a length L, wherein L is at least equal to the length of the bone anchor and wherein in the use of the anchor delivery system device the punch tip penetrates the bone creating an opening extending to a depth wherein the bone anchor is positioned adjacent above the bone opening.

13. The bone anchor delivery system device of claim 1 wherein said upper portion has an impact end for impacting the handle assembly to drive the punch through bone.

14. The bone anchor delivery system device of claim 1 wherein the spring like lock snap end when released from the slot of the upper portion allows the punch shaft to move linearly in an elongated slotted opening in the upper portion to retract the punch shaft.

15. The bone anchor delivery system device of claim 2 wherein the punch is non-metal.

16. The bone anchor delivery system device of claim 2 wherein the punch is made of synthetic or natural non-metal material.

17. The bone anchor delivery system device of claim 2 wherein the punch is made of a plastic material.

18. The bone anchor delivery system device of claim 17 wherein the plastic material is PEEK (polyether ether ketone).

19. The bone anchor delivery system device of claim 2 wherein the punch is made of a bioabsorbable material.

20. The bone anchor delivery system device of claim 2 wherein the anchor is made of a hardened biological material composition.

21. The bone anchor delivery system device of claim 2 wherein the bone anchor is non-metal.

22. The bone anchor delivery system device of claim 2 wherein the bone anchor is made of synthetic or natural non-metal material.

23. The bone anchor delivery system device of claim 2 wherein the bone anchor is made of a plastic material.

24. The bone anchor delivery system device of claim 2 wherein the bone anchor is made of a bioabsorbable material.

25. The bone anchor delivery system device of claim 2 wherein the bone anchor is made of cortical bone.

* * * * *